United States Patent
Barth et al.

[11] Patent Number: 6,022,979
[45] Date of Patent: Feb. 8, 2000

[54] PROCESS FOR PREPARING PYRAZOLES

[75] Inventors: Thomas Barth, Ludwigshafen; Norbert Rieber, Mannheim; Klaus Erhardt, Leimen, all of Germany

[73] Assignee: BASF Aktiengesellschaft, Ludwigshafen, Germany

[21] Appl. No.: 09/352,141

[22] Filed: Jul. 13, 1999

[30] Foreign Application Priority Data

Jul. 15, 1998 [DE] Germany ............................ 198 31 656

[51] Int. Cl.⁷ .................................................. C07D 231/12
[52] U.S. Cl. .......................................................... 548/373.1
[58] Field of Search .......................................... 548/373.1

[56] References Cited

FOREIGN PATENT DOCUMENTS 481 845   3/1991   European Pat. Off. .

OTHER PUBLICATIONS

J. Org. Chem. 1955, vol. 20, 1683–1686.
Recl. Trav. Chim. Pays–Bas (1965), vol. 84, 1535–1554.

*Primary Examiner*—Robert W. Ramsuer
*Attorney, Agent, or Firm*—Keil & Weinkauf

[57] ABSTRACT

A process for preparing pyrazoles of the formula I

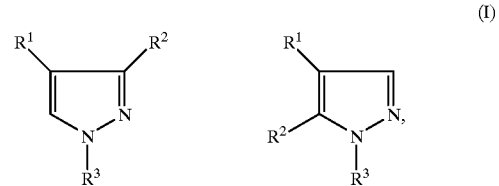

in which $R^1, R^2, R^3$ independently of one another are $C_1$- to $C_{20}$-alkyl, $C_3$- to $C_8$-cycloalkyl, or $C_7$- to $C_{20}$-aralkyl or aryl, unsubstituted or substituted by $C_1$- to $C_4$-alkyl, halogen and/or nitro, $R^1, R^3$ are additionally independently of one another hydrogen, by reacting a carbonyl compound of the formula $R^1$—$CH_2$—CO—$R^2$, in which $R^1$ and $R^2$ are as defined above in the presence of a strong base with a) formic esters of the formula H—COOR⁴, in which $R^4$ is $C_1$- to $C_8$-alkyl at from (−20) to 70° C. and a pressure of from 1 to 50 bar or b) carbon monoxide at from 0 to 100° C. and a pressure of from 1.5 to 150 bar and reacting the resulting intermediate, the hydrazines of the formula $R^3$—NH—$NH_2$, in which $R^3$ is as defined above, and an inorganic or organic acid at from 0 to 90° C. and a pressure of from 1 to 10 bar, which comprises filtering off or centrifuging off the intermediate, is described.

11 Claims, No Drawings

PROCESS FOR PREPARING PYRAZOLES

SPECIFICATION

The present invention relates to a process for preparing pyrazoles by reacting carbonyl compounds with formic esters or carbon monoxide and subsequent reaction of the intermediate with a hydrazine ($R_3$—NH—$NH_2$), where the intermediate is filtered off or centrifuged off.

J. Org. Chem. 20, (1955), 1683–1686 and Recl. Trav. Chim. Pays-Bas 84, (1965), 1535–1554 each disclose a process for preparing 3-formylbutan-2-one from formic esters or carbon monoxide, followed by reaction with hydrazine to give 3,4-dimethylpyrazole. These processes have the disadvantage that significant amounts of 3-ethylpyrazole are formed as by-product which has to be removed in a complicated manner by distillation.

Furthermore DE-A-29 22 591 and EP-A-418 845 each disclose a process for preparing pyrazoles by reacting 1,3-dicarbonyl compounds with hydrazine.

It is an object of the present invention to provide a process for preparing pyrazoles which does not require the complicated removal of isomeric pyrazoles (such as the 3-ethylpyrazole in the case of 3,4-dimethylpyrazole, for example).

We have found that this object is achieved by a novel and improved process for preparing pyrazoles of the formula I

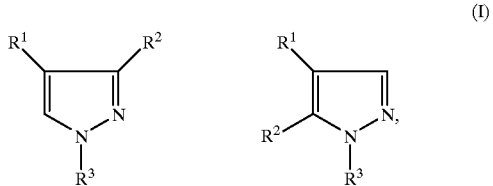

(I)

in which
$R^1, R^2, R^3$ independently of one another are $C_1$- to $C_{20}$-alkyl, $C_3$- to $C_8$-cycloalkyl, or $C_7$- to $C_{20}$-aralkyl or aryl, unsubstituted or substituted by $C_1$- to $C_4$-alkyl, halogen and/or nitro, $R^1, R^3$ are additionally independently of one another hydrogen, by reacting a carbonyl compound of the formula $R^1$—$CH_2$—CO—$R^2$, in which $R^1$ and $R^2$ are as defined above, in the presence of a strong base with a) formic esters of the formula H—$COOR^4$, in which $R^4$ is $C_1$- to $C_8$-alkyl at from (−20) to 70° C. and 1 to 50 bar or b) carbon monoxide at from 0 to 100° C. and a pressure of from 1.5 to 150 bar and reacting the resulting intermediate with hydrazines of the formula $R^3$—NH—$NH_2$, in which $R^3$ is as defined above, in the presence of an inorganic or organic acid at from 0 to 90° C. and a pressure of from 1 to 10 bar, which comprises filtering off or centrifuging off the intermediate.

The process according to the invention can be carried out as follows:

a) The carbonyl compounds of the formula $R^1$—$CH_2$—CO—$R^2$ can be reacted with formic esters of the formula H—$COOR^4$ in the presence of strong bases at from (−20) to 70° C. and a pressure of from 1 (atmospheric pressure) to 50 bar, preferably at from 0 to 60° C. and a pressure of from 1 (atmospheric pressure) to 20 bar, particularly preferably at from 20 to 50° C. and atmospheric pressure.

The molar ratio of carbonyl compound to formic ester is generally from 0.1:1 to 2:1, preferably from 0.2:1 to 1.5:1, particularly preferably from 0.3:1 to 1:1, in particular from 0.6:1 to 0.9:1. The molar ratio of carbonyl compound to strong base is generally from 0.1:1 to 2:1, preferably from 0.2:1 to 1.5:1, particularly preferably from 0.3:1 to 1:1, and in particular from 0.6:1 to 0.9:1.

b) The carbonyl compounds of the formula $R^1$—$CH_2$—CO—$R^2$ can be reacted with carbon monoxide by injecting an excess of carbon monoxide in the presence of strong bases at from 0 to 100° C. and a pressure of from 1.5 to 150 bar, preferably at from 20 to 80° C. and a pressure of from 5 to 100 bar, particularly preferably at from 30 to 70° C. and a pressure of from 10 to 40 bar.

The molar ratio of carbonyl compound to strong base is generally from 0.1:1 to 2:1, preferably from 0.2:1 to 1.5:1, particularly preferably from 0.3:1 to 1:1, in particular from 0.6:1 to 0.9:1.

In chapters 8 to 11 of Ullmann's Enzyklopädie der technician Chemie Vol. B 2 (Unit Operations I), technical processes or apparatuses are described which can be employed for separating solids:

Separation Processes: Centrifugal Sedimentation and Filtration (B 9-4 to B 9-7)

Filter Selection (B 10-55 to B 10-56)

Centrifuges (B 11-5 to B 11-19); review on centrifuges (B 11-6)

When carrying out the novel process described, particular preference is given to separation by filtration (using pressure or vacuum) or by centrifugation.

Very particular preference is given to the continuous or discontinuous use of stirred pressure nutsches, drum filters (pressure or vacuum), leaf and plate filters, pressure plate filters or centrifuges (as in scheme B 11-6, Ullmann).

Suitable strong bases are alkali metal and alkaline earth metal alkoxides or zinc alkoxides, preferably sodium methoxide, potassium methoxide, sodium ethoxide, potassium ethoxide, sodium isopropoxide, potassium isopropoxide, sodium butoxide, potassium butoxide, sodium isobutoxide, potassium isobutoxide, sodium tert-butoxide or potassium tert-butoxide, in particular methanolic sodium methoxide (NaOMe) or potassium methoxide (KOMe).

Suitable solvents are alcohols, such as methanol, ethanol, propanol, isopropanol, butanol, isobutanol or ethylene glycol, ethers such as diethyl ether, tetrahydrofuran, dioxane, preferably methanol, ethanol or tetrahydrofuran, particularly preferably methanol or ethanol.

The intermediate, generally a salt of the corresponding enolate, is reacted with hydrazines of the formula $R^3$—NH—$NH_2$, generally as hydrate, in the presence of an inorganic or organic acid at from 0 to 90° C. and a pressure of 1 (atmospheric pressure) to 10 bar, preferably at from 10 to 90° C. and a pressure of 1 (atmospheric pressure) to 5 bar, particularly preferably at from 30 to 80° C. and atmospheric pressure, in water or suitable organic solvents or mixtures thereof to give the pyrazoles (I).

The molar ratio of intermediate to hydrazine is generally from 0.25:1 to 2:1, preferably from 0.5:1 to 1.5:1, particularly preferably from 0.7:1 to 1.25:1, in particular from 0.9:1 to 1.1:1. The molar ratio of intermediate to inorganic or organic acid is generally from 0.1:1 to 3.5:1, preferably from 0.3:1 to 3:1, particularly preferably from 0.5:1 to 2.5:1, in particular from 0.7:1 to 1.8:1.

Salts of the intermediate enolates are generally lithium, sodium, potassium, magnesium, calcium or zinc salts, preferably lithium, sodium, potassium, magnesium or calcium salts, particularly preferably sodium or potassium salts, in particular sodium salts.

Suitable inorganic or organic acids are sulfuric acid, phosphoric acid, alkyl- or arylsufonic acids, formic acid, acetic acid, propionic acid, butyric acid, oxalic acid, hydrochloric acid, preferably hydrochloric acid, acetic acid, formic acid, sulfuric acid, particularly preferably sulfuric acid.

Suitable organic solvents are alcohols, such as methanol, ethanol, propanol, isopropanol, butanol, isobutanol, ethylene glycol, or ethers, such as diethyl ether, tetrahydrofuran, dioxane or dimethyl ethane, preferably methanol, ethanol, butanol, isobutanol, ethylene glycol, tetrahydrofuran or dimethoxyethane, particularly preferably methanol or ethanol. Preference is given to water and to $C_1$- to $C_4$-alcohols, such as methanol, ethanol, propanol and butanol, particularly preferably water or methanol, or mixtures thereof.

A particular embodiment of the variant a) consists in dividing the total amount of the formic ester and the strong base into two to five parts, preferably two to three parts, particularly preferably two parts, where the second part of both starting materials is generally from 15 to 50%, preferably from 20 to 45%, particularly preferably from 25 to 40%, in particular from 25 to 35%, of the total amount. For example, from 1 to 1.5 equivalents each of a carbonyl compound in a strong base and from 1.1 to 1.7 equivalents of a formic ester are initially combined, and another 0.3 to 1 equivalent each of the same formic ester and the strong base are subsequently metered in.

A particular embodiment of the subsequent processing consists in metering the intermediate, which has been filtered off and dissolved, simultaneously with the hydrazine of the formula $R^3$—NH—$NH_2$ and sulfuric acid in a molar ratio of 1: (1 to 1.5):(1.5 to 2), very particularly preferably 1:1:1.25, into methanol, water or a mixture thereof which has been initially charged.

The simultaneous metered addition of the intermediate, a hydrazine ($R^3$—NH—$NH_2$) and the inorganic or organic acid can be carried out by storing the components in separate storage containers and adding them in the desired molar ratio to the reaction container.

After isolation by filtration or centrifugation, the intermediate can be processed further either in solid form or in solution.

It is advantageous to initially charge a certain amount of a solvent or solvent mixture to the reaction container. Additionally, the reaction components can be dissolved in the same solvent.

In a variant, it is also possible to prepare initially the mixture of a hydrazine ($R^3$—NH—$NH_2$) with the inorganic or organic acid. This premix can then be metered in simultaneously with the intermediate.

The hydrazine ($R^3$—NH—$NH_2$) and the inorganic or organic acid can also be employed in the form of their acid addition salts, such as, for example, $N_2H_4 \cdot H_nX$ (n from 1 to 3), as solids or solutions.

Suitable symmetric or unsymmetric carbonyl compounds of the formula $R^1$—$CH_2$—CO—$R^2$ are, for example, acetone, methyl ethyl ketone, diethyl ketone, methyl propyl ketone, ethyl propyl ketone, dipropyl ketone, 4-methylpentan-2-one, hexan-2-one or 6-methylheptan-2-one, preferably unsymmetric carbonyl compounds, such as methyl ethyl ketone, methyl propyl ketone, ethyl propyl ketone, 4-methylpentan-2-one, hexan-2-one or 6-methylheptan-2-one, particularly preferably, methyl ethyl ketone, methyl propyl ketone or 6-methylheptan-2-one, in particular methyl ethyl ketone (butan-2-one).

Suitable formic esters of the formula H—$COOR^4$ are, for example, methyl formate, ethyl formate, propyl formate, isopropyl formate, butyl formate, isobutyl formate, pentyl formate, hexyl formate, heptyl formate or octyl formate, preferably methyl formate, ethyl formate, propyl formate, isopropyl formate, butyl formate or isobutyl formate, particularly preferably methyl formate.

Suitable hydrazines of the formula $R^3$—NH—$NH_2$ are, for example, hydrazine, monoalkyl hydrazines, monoarylhydrazines, preferably hydrazine hydrate, hydrazine, methyl hydrazine, phenyl hydrazine, or 2,4-dinitrophenylhydrazine, particularly preferably hydrazine hydrate, hydrazine, methyl hydrazine or phenyl hydrazine, in particular hydrazine hydrate or hydrazine.

The process according to the invention allows the preparation of pyrazoles (I) such as 3-methylpyrazole, 3,4-dimethylpyrazole, 3-phenylpyrazole or 3,4-diphenylpyrazole, preferably 3-methylpyrazole or 3,4-dimethylpyrazole, particularly preferably 3,4-dimethyl-1H-pyrazole.

The novel pyrazoles (I) described are, in the case that $R^3$=hydrogen, present in two tautomeric forms:

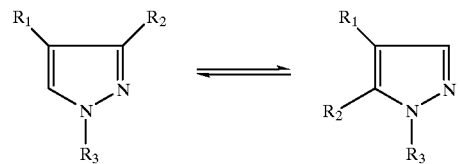

The tautomeric form of 3,4-dimethylpyrazole is 4,5-dimethylpyrazole.

If $R^3$ is not hydrogen, there are no tautomeric pyrazoles (I) present but isomeric forms. The isomer of 1,3,4-trimethylpyrazole is 1,4,5-trimethylpyrazole.

The substituents $R^1$, $R^2$, $R^3$ and $R^4$ in the pyrazoles (I), the carbonyl compounds, the formic esters and the hydrazines have the following meanings:

$R^1, R^2, R^3$ are independently of one another $C_1$- to $C_{20}$-alkyl, preferably $C_1$- to $C_8$-alkyl, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, iso-octyl, particularly preferably $C_1$- to $C_4$-alkyl, such as methyl, ethyl, n-propyl, isopropyl, n-butyl, isobutyl, sec-butyl and tert-butyl, in particular methyl, $C_3$- to $C_8$-cycloalkyl such as cyclopropyl, cyclobutyl, cyclopentyl, cyclohexyl, cycloheptyl and cyclooctyl, preferably cyclopentyl, cyclohexyl and cyclooctyl, aryl, such as phenyl, 1-naphthyl, 2-naphthyl, 1-anthryl, 2-anthryl and 9-anthryl, preferably phenyl, 1-naphthyl and 2-naphthyl, particularly preferably phenyl, $C_7$- to $C_{20}$-aralkyl, preferably $C_7$- to $C_{12}$-phenylalkyl such as benzyl, 1-phenethyl, 2-phenethyl, 1-phenylpropyl, 2-phenylpropyl, 3-phenylpropyl, 1-phenylbutyl, 2-phenyl-butyl, 3-phenyl-butyl and 4-phenyl-butyl, particularly preferably benzyl, 1-phenethyl and 2-phenethyl, aryl which is substituted by $C_1$- to $C_4$-alkyl and/or halogen and/or nitro, such as phenyl which is mono- to trisubstituted by $C_1$- to $C_4$-alkyl and/or halogen and/or nitro (but not by more than two nitro groups), preferably 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6- trimethylphenyl, 2,4,6-trimethylphenyl, 2-ethylphenyl, 3-ethylphenyl, 4-ethylphenyl, 2-n-propylphenyl, 3-n-propylphenyl, 4-n-propylphenyl, 2-chlorophenyl, 3-chlorophenyl, 4-chlorophenyl, 2,4-dichlorophenyl, 2,5-dichlorophenyl, 2,6-dichlorophenyl, 3,4-dichlorophenyl, 3,5-dichlorophenyl, 2,3,4-trichlorophenyl, 2,3,5-trichlorophenyl, 2,3,6-trichlorophenyl, 2,4,6-trichlorophenyl, 2-bromophenyl, 3-bromophenyl, 4-bromophenyl, 2,4-dibromophenyl, 2,5-dibromophenyl, 2,6-dibromophenyl, 3,4-dibromophenyl, 3,5-dinitrophenyl, 2,3,4-tribromophenyl, 2,3,5-tribromophenyl, 2,3,6-tribromophenyl, 2,4,6-tribromophenyl, 2-nitrophenyl, 3-nitrophenyl, 4-nitrophenyl, 2,4-dinitrophenyl, 2,5-dinitrophenyl, 2,6-dinitrophenyl, 3,4-dinitrophenyl or 3,5-dinitrophenyl, preferably 4-methylphenyl, 2,4-dimethylphenyl, 4-chlorophenyl, 2,4-dichlorophenyl, 4-nitrophenyl or 2,4-dinitrophenyl, particularly preferably 4-methylphenyl, 4-chlorophenyl or 4-nitrophenyl, $C_7$- to $C_{20}$-aralkyl which is substituted by $C_1$- to $C_4$-alkyl and/or halogen and/or nitro, such as $C_7$- to $C_{12}$-phenalkyl which is mono- to trisubstituted by $C_1$- to $C_4$-alkyl and/or halogen and/or nitro (but not by more than two nitro groups), preferably 2-methylphenylmethyl, 3-methylphenylmethyl, 4-methylphenylmethyl, 2,4-dimethylphenylmethyl, 2,5-dimethylphenylmethyl, 2,6-dimethylphenylmethyl, 3,4-dimethylphenylmethyl, 3,5-dimethylphenylmethyl, 2,3,4-trimethylphenylmethyl, 2,3,5-trimethylphenylmethyl, 2,3,6-trimethylphenylmethyl, 2,4,6-trimethylphenylmethyl, 2-ethylphenylmethyl, 3-ethylphenylmethyl, 4-ethylphenylmethyl, 2-n-propylphenylmethyl, 3,2-n-propylphenylmethyl, 4-n-propylphenylmethyl, 2-chlorophenylmethyl, 3-chlorophenylmethyl, 4-chlorophenylmethyl, 2,4-dichlorophenylmethyl, 2,5-dichlorophenylmethyl, 2,6-dichlorophenylmethyl, 3,4-dichlorophenylmethyl, 3,5-dichlorophenylmethyl, 2,3,4-trichlorophenylmethyl, 2,3,5-trichlorophenylmethyl, 2,3,6-trichlorophenylmethyl, 2,4,6-trichlorophenylmethyl, 2-bromophenylmethyl, 3-bromophenylmethyl, 4-bromophenylmethyl, 2,4-dibromophenylmethyl, 2,5-dibromophenylmethyl, 2,6-dibromophenylmethyl, 3,4-dibromophenylmethyl, 3,5-dinitrophenylmethyl, 2,3,4-tribromophenylmethyl, 2,3,5-tribromophenylmethyl, 2,3,6-tribromophenylmethyl, 2,4,6-tribromophenylmethyl, 2-nitrophenylmethyl, 3-nitrophenylmethyl, 4-nitrophenylmethyl, 2,4-dinitrophenylmethyl, 2,5-dinitrophenylmethyl, 2,6-dinitrophenylmethyl, 3,4-dinitrophenylmethyl, 3,5-dinitrophenylmethyl or 2,4,6-trinitrophenylmethyl, preferably 2,4,6-trichlorophenyl, 2,4,6-trimethylphenyl or 2,4,6-trinitrophenylmethyl, particularly preferably 2,4,6-trichlorophenylmethyl, $R^1, R^3$ are independently of one another hydrogen $R^4$ $C_1$- to $C_8$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, preferably $C_1$- to $C_4$-alkyl such as methyl, ethyl, n-propyl, isopropyl, n-butyl, isobutyl, sec-butyl and tert-butyl, particularly preferably methyl.

The pyrazoles I which can be prepared by the process according to the invention are useful starting materials for preparing dyes, drugs and, in particular, crop protection agents. 3,4-Dimethylpyrazole or acid addition salts thereof are effective nitrification inhibitors.

EXAMPLES

The total yields of 3,4-dimethyl-1H-pyrazole are based on butan-2-one.

Example 1

Preparation of 3,4-dimethyl-1H-pyrazole with Filtration of the Intermediate

At 30° C., a mixture of 36 g (0.5 mol) of butan-2-one and 33 g (0.55 mol) of methyl formate were metered into 90 g (0.5 mol) of a 30% strength solution of sodium methoxide in methanol, the mixture was stirred at 30° C. for 2 h, 27 g (0.15 mol) of sodium methoxide solution and 9 g (0.15 mol) of methyl formate were subsequently metered in, and the mixture was stirred at room temperature for approximately 16 h. The resulting suspension was filtered off, giving 50 g (67%) of sodium formyl butanone (content: 81.4%).

50 g (0.33 mol) of the solid sodium formyl butanone were dissolved in 200 ml of water (content of the solution: 16.3%) and this mixture was initially charged at room temperature, 21 g (0.21 mol) of 96% strength sulfuric acid and subsequently 16.7 g (0.33 mol) of hydrazine hydrate (100%) were added dropwise, and the mixture was stirred at room temperature for approximately 16 h. The reaction discharge was adjusted to pH 8.1 using 20% strength aqueous sodium hydroxide solution. Phase separation gave 19.2 g (61%) of 3,4-dimethyl-1H-pyrazole and 0.22 g (0.7%) of 3-ethyl-1H-pyrazole. The total yield of 3,4-dimethyl-1H-pyrazole over both steps was 40%.

Comparative Example 1

Preparation of 3,4-dimethyl-1H-pyrazole Using the Total Intermediate Suspension without Filtration The reaction was carried out by the method of Example 1, but the resulting suspension, which contained 0.41 mol of sodium formyl butanone (yield: 82%), was not filtered but adjusted directly to pH=7 using 50% strength sulfuric acid and reacted with hydrazine hydrate (100%) by the method of example 1. During the reaction, the pH was maintained at pH=7 to 8 using 50% strength sulfuric acid. The reaction discharge was adjusted to pH 8.1 using 20% strength aqueous sodium hydroxide solution and evaporated. The residue was taken up in 150 ml of water and the phases were separated, giving 25.3 g (63%) of 3,4-dimethyl-1H-pyrazole and 2.6 g (3%) of 3-ethyl-1H-pyrazole. The total yield of 3,4-dimethyl-1H-pyrazole over both steps was 52%.

Example 2

Preparation of 3,4-dimethyl-1H-pyrazole with Filtration of the Intermediate and Simultaneous Metered Addition During the Reaction of the Intermediate.

The reaction was carried out by the method of Example 1, but the sodium formyl butanone (0.2 mol) was, dissolved in water (content of the solution: 15.4%), at room temperature simultaneously with 96% strength sulfuric acid (0.125 mol) and hydrazine hydrate (80%) (0.2 mol) added dropwise to 50 ml of methanol. The pH was adjusted to 8.1 and the methanol was then evaporated. Phase separation, extraction of the aqueous phase with 2×50 ml of tert-butyl methyl ether and removal of the solvent gave 17.2 g (90%) of 3,4-dimethyl-1H-pyrazole. 3-ethyl-1H-pyrazole could not be detected. The total yield of 3,4-dimethyl-1H-pyrazole over both steps was 60%.

Comparative Example 2

Preparation of 3,4-dimethyl-1H-pyrazole without Filtration of the Intermediate and with Simultaneous Metered Addition During the Reaction of the Intermediate.

The reaction was carried out by the method of Example 1, but the resulting solution was dissolved in 60 ml of water and not filtered. This gave a solution having a content of sodium formyl butanone of 20.5% (yield: 82%). A 0.2 mol equivalent of this sodium formyl butanone solution was, simultaneously with 96% strength sulfuric acid (0.125 mol) and hydrazine hydrate (80%) (0.2 mol), reacted by the method of Example 2. Work-up was carried out as in Example 2. This gave 14.5 g (79%) of 3,4-dimethyl-1H-pyrazole and 1.7 g (9.5%) of 3-ethyl-1H-pyrazole. The total yield of 3,4-dimethyl-1H-pyrazole over both steps was 65%.

Example 3

Carbonylation of butan-2-one 90 g (0.5 mol) of a 30% strength solution of sodium methoxide in methanol and 17 g (0.53 mol) of methanol were filled into a steel autoclave (300 ml) and heated to 70° C., and 10 bar of carbon monoxide (CO) were injected. A carbon monoxide pressure of 10 bar was maintained while the autoclave cooled with stirring to room temperature. After the carbon monoxide uptake had ended, 36.1 g (0.5 mol) of butan-2-one were added at atmospheric pressure, and 40 bar of carbon monoxide were injected until the pressure remained constant.

After the reaction had ended, the reaction discharge was taken up in toluene and filtered off. This gave 50 g (78%) of a colorless solid, 94.7% of which consisted, according to titration, of the desired sodium enolate.

Comparative Example 3

(by the method of Recl. Trav. Chim. Pays-Bas 84 (1965), 1552)

3.3 g (64 mmol) of sodium methoxide were initially charged in 50 ml of dimethoxyethane, 4.5 g (62 mmol) butan-2-one and 3.7 g (62 mmol) of methyl formate were added, and the mixture was stored at room temperature overnight. Filtration and washing of the filter residue with 2×10 ml of diethyl ether gave 7.3 g (63%, 39 mmol) of sodium enolate.

6.5 g (34.7 mmol) of the sodium enolate were dissolved in 40 ml of water and admixed with 3.7 g (62 mmol) of glacial acetic acid, and 3.1 g (62 mmol) of hydrazine hydrate were added dropwise. The mixture was heated under reflux for 2 h and the biphasic reaction discharge was then adjusted to pH=7 using glacial acetic acid and extracted once with 20 ml of methyl tert-butyl ether, and the organic phase was washed once with 20 ml of 10% strength sodium carbonate solution and dried over sodium sulfate. Removal of the solvent gave 2.1 g of a mixture of 95% of 3,4-dimethyl-1H-pyrazole (20.8 mmol, 60%) and 4% of 3-ethyl-1H-pyrazole (determined by HPLC). The total yield of 3,4-dimethylpyrazole over both steps was 38%.

We claim:

1. A process for preparing pyrazoles of the formula I

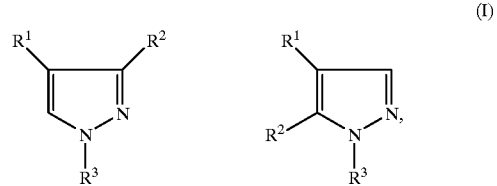

in which $R^1, R^2, R^3$ independently of one another are $C_1$- to $C_{20}$-alkyl, $C_3$- to $C_8$-cycloalkyl, or $C_7$- to $C_{20}$-aralkyl or aryl, unsubstituted or substituted by $C_1$- to $C_4$-alkyl, halogen and/or nitro, and $R^1, R^3$ are additionally independently of one another hydrogen, by reacting a carbonyl compound of the formula $R^1$—$CH_2$—$CO$—$R^2$, in which $R^1$ and $R^2$ are as defined above in the presence of a strong base with a) formic esters of the formula H—$COOR^4$, in which $R^4$ is $C_1$- to $C_8$-alkyl at from (−20) to 70° C. and a pressure of from 1 to 50 bar or b) carbon monoxide at from 0 to 100° C. and a pressure of from 1.5 to 150 bar and reacting the resulting intermediate with hydrazines of the formula $R^3$—NH—$NH_2$, in which $R^3$ is as defined above, in the presence of an inorganic or organic acid at from 0 to 90° C. and a pressure of from 1 to 10 bar, which comprises filtering off or centrifuging off the intermediate.

2. A process for preparing pyrazoles I as claimed in claim 1, wherein $R^1, R^2, R^3$ independently of one another are $C_1$- to $C_8$-alkyl, cyclopentyl, cyclohexyl, or $C_7$- to $C_{12}$-aralkyl or phenyl, unsubstituted or mono- to trisubstituted by $C_1$- to $C_4$-alkyl, halogen and/or nitro and $R^1, R^3$ are additionally independently of one another hydrogen.

3. A process for preparing pyrazoles I as claimed in claim 1, wherein $R^1, R^2$ independently of one another are $C_1$- to $C_4$-alkyl, cyclopentyl, cyclohexyl, phenyl or $C_7$- to $C_{12}$-aralkyl and $R^1, R^3$ are additionally independently of one another hydrogen.

4. A process for preparing pyrazoles I as claimed in claim 1, wherein $R^1, R^2$ are methyl and $R^3$ is hydrogen.

5. A process for preparing pyrazoles I as claimed in claim 1, wherein the reaction a) with formic esters is carried out at from 0 to 60° C. and a pressure of from 1 to 20 bar.

6. A process for preparing pyrazoles I as claimed in claim 1, wherein in the reaction of carbonyl compounds with formic esters the total amount of base and formic ester is divided into two to five parts and added successively to the reaction mixture.

7. A process for preparing pyrazoles I as claimed in claim 1, wherein in the reaction of carbonyl compounds with formic esters the total amount of base and formic ester is divided into two to three parts and added successively to the reaction mixture.

8. A process for preparing pyrazoles I as claimed in claim 1, wherein in the reaction of carbonyl compounds with formic esters the total amount of base and formic ester is divided into two and added successively to the reaction mixture.

9. A process for preparing pyrazoles I as claimed in claim 1, wherein the reaction b) with carbon monoxide is carried out at from 20 to 80° C. and a pressure of from 5 to 100 bar.

10. A process for preparing pyrazoles I as claimed in claim 1, wherein the reaction with hydrazines is carried out at from 10 to 90° C. and a pressure of from 1 to 20 bar.

11. A process for preparing pyrazoles I as claimed in claim 1, wherein the intermediate, a hydrazine ($R^3$—NH—$NH_2$) and the inorganic or organic acid are metered in simultaneously.

* * * * *